United States Patent
Thomas et al.

(10) Patent No.: US 10,898,265 B2
(45) Date of Patent: *Jan. 26, 2021

(54) MICROWAVE ABLATION APPLICATORS

(71) Applicant: Gyrus Medical Limited, Cardiff (GB)

(72) Inventors: Tudor Thomas, Cardiff (GB); Lewis Jones, Cardiff (GB); David Nicholas Williams, Caerphilly (GB)

(73) Assignee: Gyrus Medical Limited, Cardiff (GB)

( * ) Notice: Subject to any disclaimer, the term of this patent is extended or adjusted under 35 U.S.C. 154(b) by 388 days.

This patent is subject to a terminal disclaimer.

(21) Appl. No.: 15/870,817

(22) Filed: Jan. 12, 2018

(65) Prior Publication Data
US 2018/0214206 A1   Aug. 2, 2018

(30) Foreign Application Priority Data

Jan. 27, 2017 (GB) .................................. 1701362.4

(51) Int. Cl.
*A61B 18/18* (2006.01)
*A61B 18/00* (2006.01)
*A61M 25/00* (2006.01)

(52) U.S. Cl.
CPC ...... *A61B 18/1815* (2013.01); *A61B 2018/00083* (2013.01); *A61B 2018/00577* (2013.01); *A61B 2018/1838* (2013.01); *A61B 2018/1869* (2013.01); *A61B 2018/1892* (2013.01); *A61M 25/005* (2013.01)

(58) Field of Classification Search
CPC ...... A61B 18/1815; A61B 2018/00577; A61B 2018/1869; A61B 2018/00083; A61B 2018/1838; A61B 2018/1892; A61B 2018/1861; A61B 18/00–28; A61B 2018/00005–266; A61M 25/005
See application file for complete search history.

(56) References Cited

U.S. PATENT DOCUMENTS

| 9,161,814 B2* | 10/2015 | Brannan | A61B 18/1815 |
| 2014/0171932 A1* | 6/2014 | Dunning | H05B 6/6408 |
| | | | 606/33 |
| 2019/0099219 A1* | 4/2019 | Thomas | A61B 18/1815 |

FOREIGN PATENT DOCUMENTS

EP   2777590 A1   9/2014

OTHER PUBLICATIONS

Harris, Tom, "UK Search Report", prepared for application No. 1701362.4, dated May 31, 2017, 5 pages.

* cited by examiner

*Primary Examiner* — Joseph A Stoklosa
*Assistant Examiner* — Caitlyn E May
(74) *Attorney, Agent, or Firm* — Winstead PC (57) ABSTRACT

A shaft assembly for a microwave ablation applicator which includes a shaft assembly and an antenna assembly located within the shaft assembly is disclosed. The shaft assembly comprises an elongate shaft which extends from a first end to a second end thereof, and which defines therein a hollow inner volume and a longitudinal axis of the antenna assembly, and an applicator tip mounted on the second end of the elongate shaft. The applicator tip defines an annular slot with which the second end of the elongate shaft engages. At least part a portion of the second end of the shaft is of a fibre reinforced plastics material having a plurality of elongate fibres bound in a plastics material, at least some of the fibres extending at least partially circumferentially around the annular slot of the applicator tip.

15 Claims, 5 Drawing Sheets

MICROWAVE ABLATION APPLICATORS

CROSS-REFERENCE TO RELATED APPLICATIONS

This application claims priority to and incorporates by reference the entire disclosure of International Application No. GB 1701362.4, filed on Jan. 27, 2017.

The present invention relates to microwave ablation applicators, and, in particular, to shaft assemblies for such applicators.

BACKGROUND OF THE INVENTION

In the treatment of tumours, for example tumours caused by a disease such as cancer, it is known to use microwave ablation techniques to ablate the tumour. Such microwave ablation techniques typically ablate the targeted tissue by delivering a controlled amount of microwave energy into the tumour.

Minimally-Invasive techniques for delivering such microwave energy have been shown to be effective in the treatment of tumours. In a minimally-invasive technique, a microwave emitter is inserted directly into a point of treatment, either using a normal shaft orifice or via percutaneous insertion. Such minimally-invasive procedures and devices provide a means of treating tumours in patients who either cannot undergo other forms of treatment (e.g. radiotherapy, surgical resection, chemotherapy) or where ablation is preferred as a therapy.

The microwave emitter is provided in a microwave ablation applicator. One type of commonly used microwave ablation applicator has an elongate shaft assembly that houses an antenna assembly. The shaft assembly is provided by a shaft in the form of a thin walled cylinder which extends from a proximal end to a distal end thereof and defines an inner volume therein, and an applicator tip which is carried by, and closes, the distal end of the shaft. The applicator tip has a shape which is appropriate for insertion in to the tissue being treated, and which provides suitable electromagnetic properties. One particular exemplary antenna assembly includes a dipole antenna element located towards the distal end of the shaft in the inner volume of the shaft, adjacent the applicator tip. The antenna assembly also includes a coaxial conductor which extends along the inner volume of the shaft in order to connect the dipole antenna element to a source of microwave energy.

It is desirable for a microwave ablation applicator to be narrow and lightweight, but with high stiffness. For this reason, composite fibre-resin materials (fibre reinforced plastics, FRP, materials) have been considered as appropriate for the shaft. However, some fibre reinforced plastics materials result in undesirably thick side walls for the shaft leading to an undesirably large overall outer diameter of the shaft. Conversely, a desirably narrow shaft of the same material would result in lower than required stiffness of the shaft. Carbon fibre reinforced plastics (CFRP) materials enable the provision of a narrower side wall, and hence narrower shaft overall, due to the higher strength and stiffness of a CFRP material compared with other FRP materials. However, CFRP materials contain carbon fibres that are electrically conductive, and are, therefore, not suitable for attachment to an electrically conductive tip of the antenna assembly, since the conductivity of the carbon would prevent radiation of microwave energy from the applicator tip.

In addition, previously-considered techniques for the attachment of the applicator tip to an assembly shaft of a fibre reinforced material have not provided an attachment that is sufficiently strong to ensure that the tip does not separate from the shaft when the assembly is in use.

It is, therefore, desirable to provide a shaft assembly that is able to address the drawbacks of the previously-considered designs.

SUMMARY OF THE INVENTION

According to a first aspect of the present invention, there is provided a shaft assembly for a microwave ablation applicator which includes a shaft assembly and an antenna assembly located within the shaft assembly, the shaft assembly comprising an elongate shaft which extends from a first end to a second end thereof, and which defines therein a hollow inner volume and a longitudinal axis of the antenna assembly; and an applicator tip mounted on the second end of the elongate body, wherein the applicator tip of the shaft assembly defines an annular slot with which the second end of the elongate shaft engages, and wherein at least a part of the shaft is of a fibre reinforced plastics material having a plurality of elongate fibres bound in a plastics material, at least some of the fibres extending at least partially circumferentially in and around the annular slot of the applicator tip.

In one example, at least some of the fibres extend along the elongate shaft substantially parallel to the longitudinal axis of the antenna assembly, those fibres extending into and at least partially around the annular slot in the applicator tip.

In such an example, at least some of the fibres may extend substantially circumferentially fully around the annular slot in the applicator tip.

In one example. substantially all of the fibres may extend into the annular slot.

In such an example, substantially all of the fibres may extend substantially circumferentially fully around the annular slot in the applicator tip.

In one example, the fibre reinforced plastics material includes carbon fibres, and the applicator tip is of an electrically insulating material.

In one example, the fibres that extend circumferentially around the annular slot of the applicator tip are distinct from the elongate fibres of the shaft to provide retaining fibres for the assembly. In such an example, the retaining fibres may extend circumferentially around the annular slot radially inside the fibres of the shaft, or may extend circumferentially around the annular slot radially outside the fibres of the shaft. In one example, the retaining fibres are bound in the plastics material of the shaft fibres.

In one example, the applicator tip comprises a base portion which engages an internal surface of the body, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion.

In such an example, the base portion, intermediate portion, and distal portion of the applicator tip are provided by a single contiguous component.

According to a second aspect of the present invention, there is provided a microwave ablation applicator comprising a shaft assembly according to the first aspect of the present invention, and an antenna assembly including an elongate coaxial conductor for connection to a source of microwave energy, the coaxial conductor extending from the first end of the shaft of the shaft assembly towards the second end of the shaft through the inner volume, the coaxial conductor having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the coaxial conductor at a distal end thereof towards the second end of the body, and a dipole tip portion which extends from the feed point of the coaxial conductor assembly towards the applicator tip of the shaft assembly, and which is electrically connected with the inner conductor of the coaxial conductor assembly, wherein the applicator tip of the shaft assembly defines an annular slot with which the second end of the elongate shaft engages, and wherein at least a part of the shaft is of a fibre reinforced plastics material having a plurality of elongate fibres bound in a plastics material, at least some of the fibres extending into the annular slot of the applicator tip, and extending at least partially circumferentially around the annular slot of the applicator tip.

According to a third aspect of the present invention, there is provided an applicator tip for use with a shaft assembly according to the first aspect of the present invention, or for use with a microwave ablation applicator according to the second aspect of the present invention, wherein the applicator tip comprises a base portion for engagement with an internal surface of the body, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion.

DETAILED DESCRIPTION OF THE PREFERRED EMBODIMENTS

Figure 1:
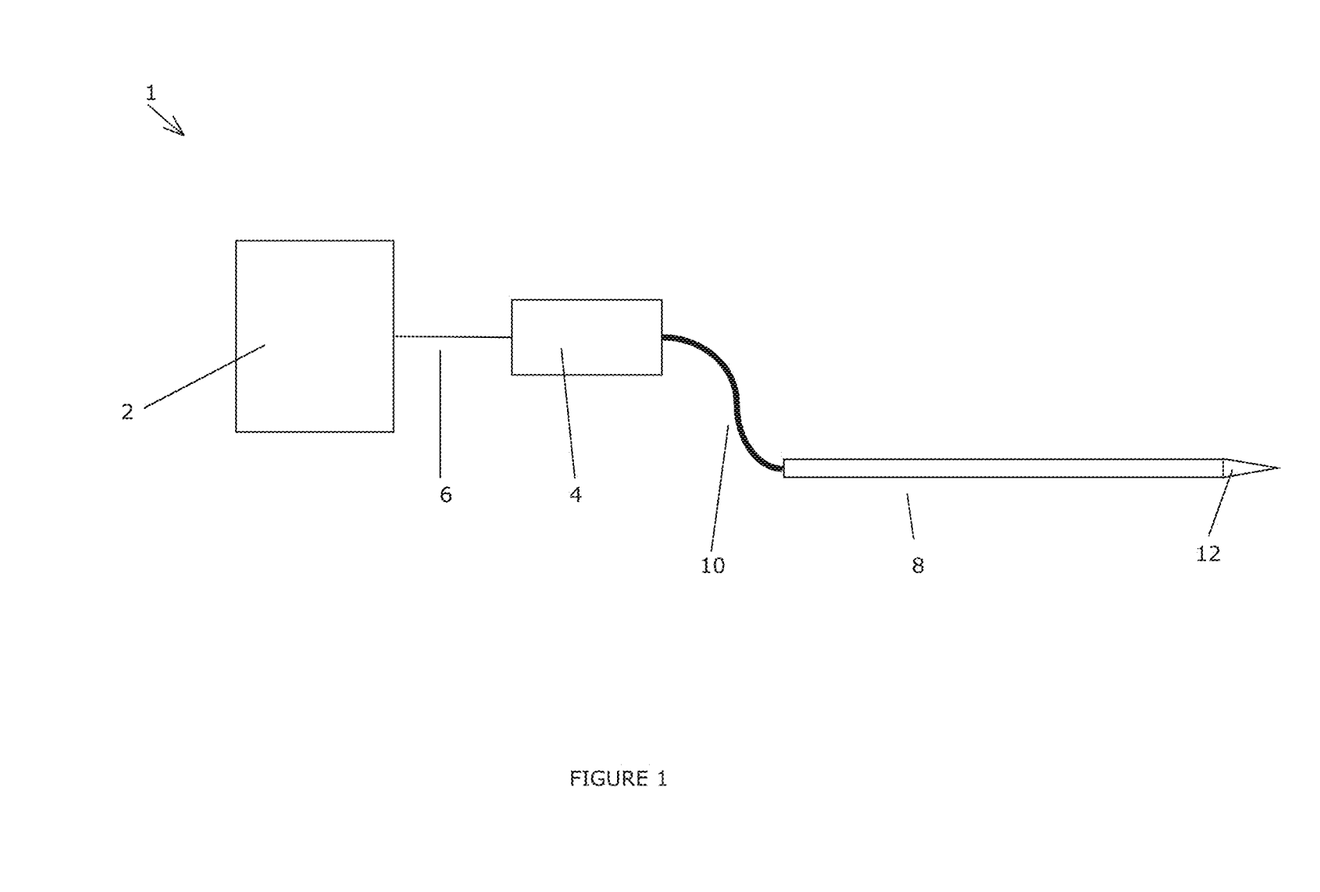
FIG. 1 is a schematic block diagram of a microwave ablation system.

FIG. 1 is a schematic diagram illustrating a microwave ablation system 1 comprising a controller unit 2, and a microwave power generator 4 which is connected to the controller via a control connection 6. An ablation applicator 8 is connected to the microwave power generator 4 via a power connection 10. The ablation applicator 8 includes a shaft assembly having a shaft which carries an applicator tip 12 which aids insertion of the ablation applicator 8 into the tissue being treated, and enables a desired output pattern of microwave energy from the ablation applicator 8.

The controller unit 2 is operable to control the power generator 4 to supply the correct magnitude and frequency of microwave energy to the ablation applicator 8. Different control schemes are known in the art, and will not be described here for the sake of clarity. The present invention is concerned with the design of the ablation applicator 8, and such as an ablation applicator 8 may be used with any appropriate control scheme and control hardware.

Figure 2:
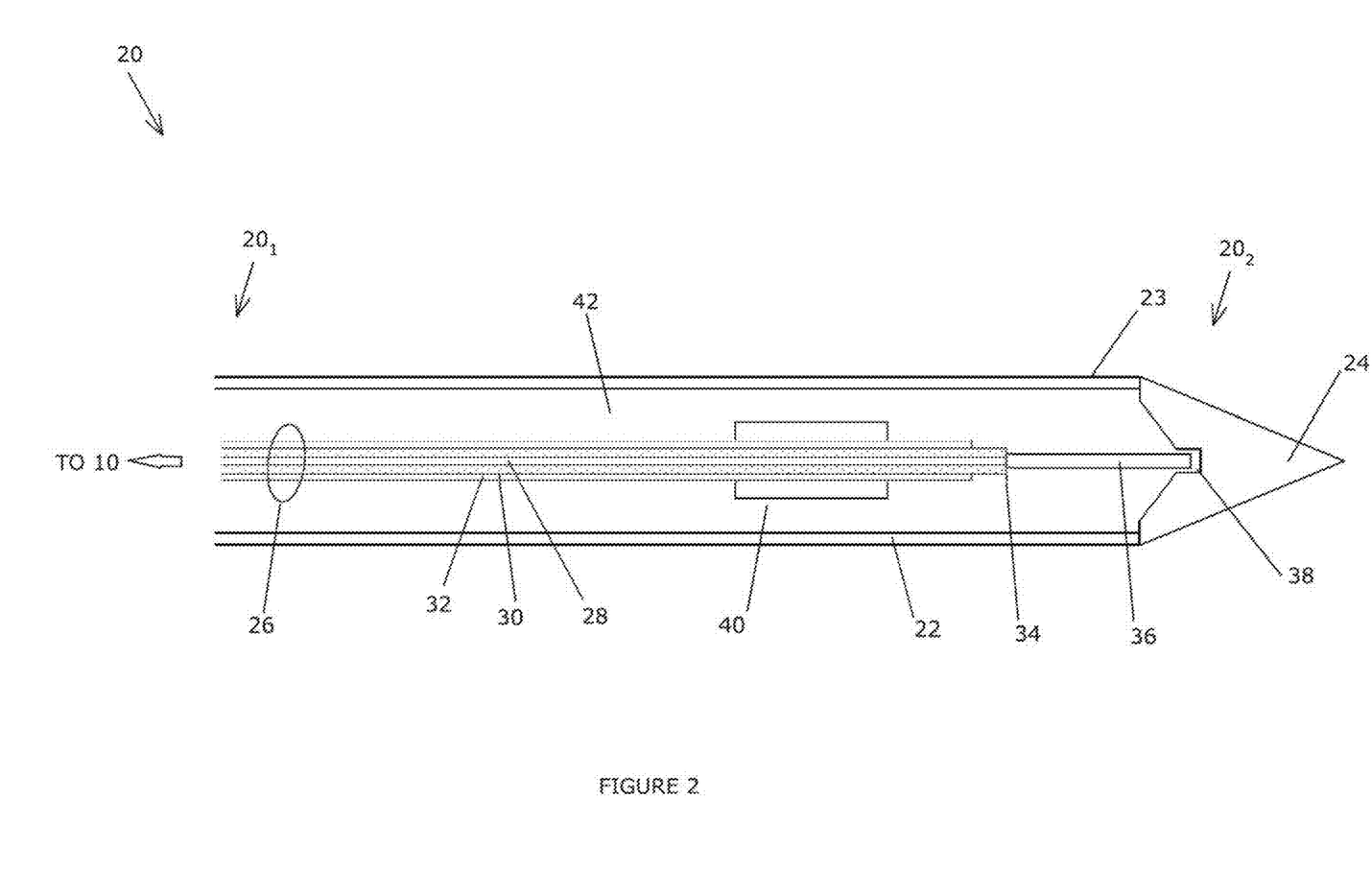
FIG. 2 is a cross sectional side view of part of a microwave ablation applicator.

FIG. 2 is a cross-sectional view of part of an ablation applicator 20 which comprises a shaft assembly and an antenna assembly. The shaft assembly includes a shaft 22, preferably cylindrical in form, which extends from a first (proximal) end $20_1$ to a second (distal) end $20_2$, and defines a longitudinal axis of the assembly and applicator. The second (distal) end $20_2$ of the shaft carries an applicator tip 24 for insertion into the tissue being treated. The shaft 22 defines an inner volume, in which most of the other components of the applicator are housed. The shaft 22 provides the applicator with the necessary rigidity for insertion into the tissue being treated. The shaft 22 is of a substantially rigid composite material, and is typically 1.5 to 3 mm in diameter.

The shaft assembly includes an applicator tip 24 which is attached to the second end $20_2$ of the shaft 22, so as to close off the inner volume at the second end. The applicator tip 24 is preferably a faceted trocar and has a relatively sharp distal end point. The applicator tip 24 is designed to be suitable for insertion into the tissue being treated, and partly to affect the transmission pattern for microwave energy into that tissue. The tip 24 also forms a water tight seal to the internal volume of the shaft 22. Attachment of the applicator tip 24 to the shaft 22 in accordance with the principles of the present invention will be described below with reference to FIGS. 3 and 4.

The antenna assembly comprises a coaxial conductor 26 which extends along the inner volume of the shaft 22 from the first end $20_1$ towards the second end $20_2$. The coaxial conductor 26 is connectable, at a proximal end thereof, to the microwave energy generator 4 of FIG. 1. The coaxial conductor 26 comprises an inner conductor 28 of an electrically conductive material such as copper. Surrounding the inner conductor 28 is a dielectric layer 30 which extends along the inner conductor 28, radially outwardly thereof. The dielectric layer 30 is of any appropriate dielectric material. Surrounding the dielectric layer 30, is an outer conductor 32, which is of an electrically conductive material such as copper. The outer conductor 32 extends along an outer surface of the dielectric layer 30, radially outwards thereof. Typically, the inner conductor 28 is a wire having a circular cross section, such that the dielectric layer 30 is a cylinder of dielectric material surrounding an outer surface of the inner conductor 28. The outer conductor 32 is then formed by a cylinder of electrically conductive material surrounding an outer surface of the dielectric layer 30.

The dielectric layer 30 extends along the complete length of the inner conductor 28 to the distal end thereof. The outer conductor 32 stops short of the distal end of the inner conductor 28 and dielectric layer 30, and so is spaced apart longitudinally from that end point. The distal end of the coaxial conductor thereby defines a signal feed-point 34.

A dipole antenna element 36 extends longitudinally from the distal end (i.e. from the signal feedpoint 34) of the coaxial conductor 36 into a reception recess 38 in the applicator tip 24. The dipole antenna element 36 is connected to receive microwave energy from a microwave energy source by the coaxial conductor 26. The dipole antenna element 36 is arranged to emit microwave energy in a predetermined output pattern.

The reception recess 38 of the applicator tip 24 is located centrally with respect to the longitudinal axis of the assembly within the applicator tip 24. The reception recess 38 is designed so as to locate centrally the dipole tip portion 36 in the tip 24. The tip material is chosen for it mechanical and electrical properties, which have to be considered in the design.

A dielectric fluid may be provided within the inner volume of the shaft 20 in order to provide a dielectric element in the microwave design and also provide a cooling fluid for the antenna assembly. This fluid may be isotonic saline or deionised water.

In the example shown in FIG. 2, an electromagnetic choke assembly 40 is located within the shaft 22, around the coaxial conductor 26, spaced apart from the distal end of the coaxial conductor 26. It will be readily understood that the choke assembly is optional, depending on the design requirements of the assembly. The choke assembly 40 comprises a choke dielectric element 42 which extends around a portion of the outer conductor 32. In the case when the coaxial conductor 26 has a circular cross section, the choke dielectric element 42 is in the form of a cylinder of dielectric material surrounding an outer surface of the outer conductor 32 of the coaxial conductor 26. The choke dielectric has a proximal end towards the first end $20_1$ of the shaft 22 and a distal end towards the second end $20_2$ of the shaft 22. The length of the choke dielectric element 42 along the coaxial conductor 26 is determined by the desired electromagnetic/electrical characteristics of the choke assembly 40.

Figure 3:
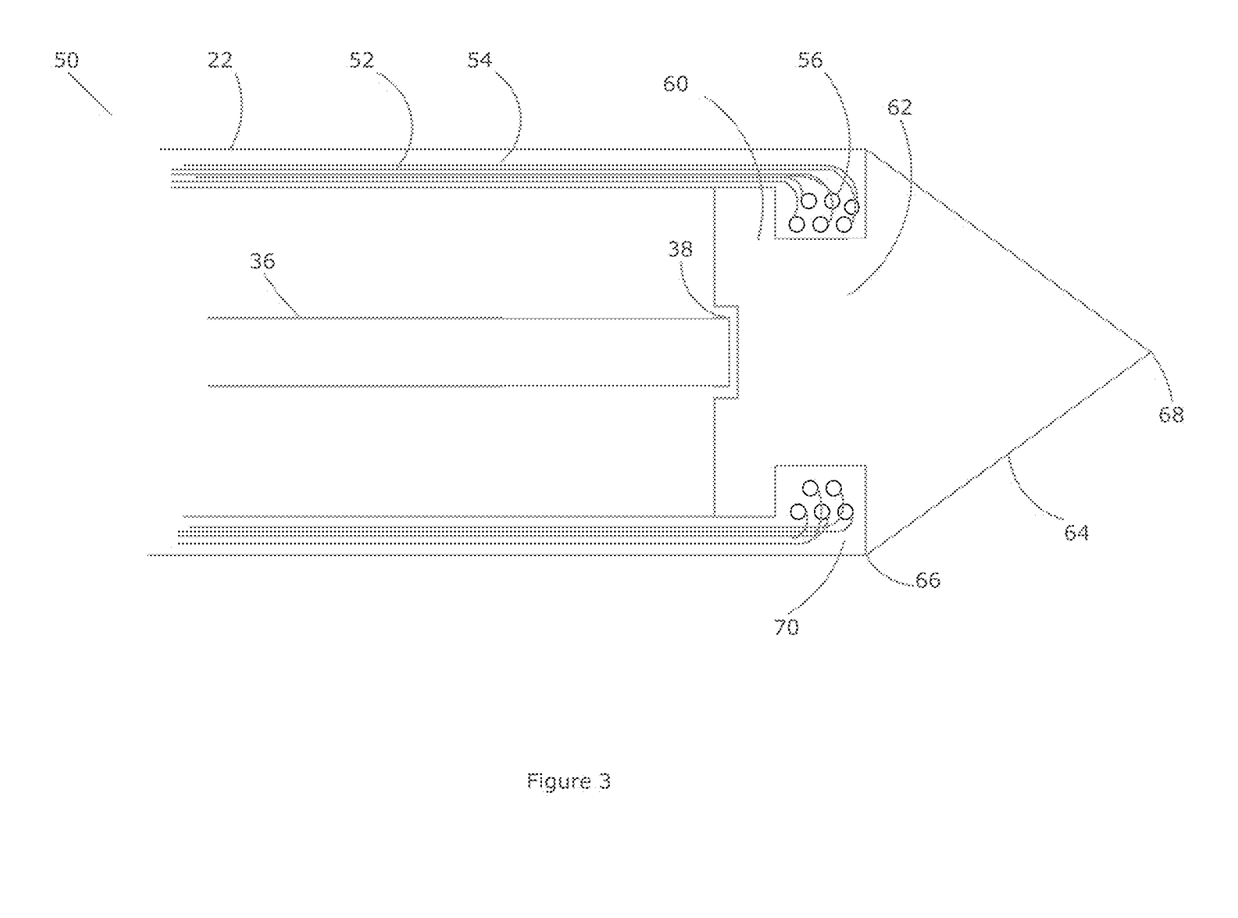
FIGS. 3, 4 and 5 are cross sectional side views of respective distal parts of microwave ablation applicators embodying respective aspects of the present invention, and including shaft assemblies and applicator tips embodying respective other aspects of the present invention.

FIG. 3 illustrates, in side cross-sectional view, a distal end portion 50 of an ablation applicator embodying one aspect of the present invention. The distal end portion 50 comprises the distal end region of the shaft 22 to which the applicator tip 24 is attached. The dipole antenna element 36 extends through the distal end portion 50, to engage with the reception recess 38 of the applicator tip 24, as described with reference to FIG. 2 above.

In an embodiment of the present invention, the shaft 22 is of a fibre reinforced plastics material. Suitable fibre reinforced plastics materials include those using fibres of glass, aramid or carbon, bound in a polymer material such as an epoxy, vinylester or polyester thermosetting plastics material. The shaft 22, therefore, includes a plurality of fibres 52 bound in the plastics material 54.

The applicator tip 24 has an outer shape that matches cross section of the shaft 22, and is, therefore, preferably circular in cross section. The applicator tip 24 has a proximal base portion 60 which engages with the inner surface of the shaft 22, and which includes the reception recess 38. The applicator tip 24 has an intermediate portion 62 which extends from the base portion 60 towards a distal end of the tip 24. The intermediate portion 60 has an outer diameter smaller than that of the base portion 60. A distal portion 64 of the applicator tip 24 extends from the intermediate portion 62.

It will be readily appreciated that the base portion 60, intermediate portion 62 and distal portion 64 of the applicator tip 24 are preferably provided by a single contiguous component.

The distal portion 64 extends, and narrows, from an engagement portion 66 to a tip 68. The engagement portion 66 has an outer diameter substantially equal to that of the shaft 22, such that the shaft assembly has a substantially continuous outer profile, to aid insertion and retraction of the applicator. The base portion 60, intermediate portion 62 and distal portion 64 define an annular slot 70 therebetween. The annular slot 70 is defined between a distal surface of the base portion 60 and a proximal surface of the distal portion 64, and extending circumferentially around an outer surface of the intermediate portion 62.

The material of the shaft 22 extends into the annular slot 70 in order to secure the applicator tip 24 to the shaft 22. In one example, at least some of the fibres 52 have portions 56 thereof that extend into the annular slot 70 of the applicator tip 24, and extend at least partially circumferentially around the slot. The plastics material 54 extends into the annular slot 70.

In a preferred example, the fibres 52 of the shaft 22 extend individually substantially parallel to the longitudinal axis of the assembly to the applicator tip 24, such that the shaft is formed of a unidirectional fibre reinforced material. Each fibre 52 extends 56 into the annular slot 70 of the applicator tip 24. The fibres 52, 56 may extend fully, partially or multiple times circumferentially around the annular slot 70. The fibres 52, 56 are preferably looped around the intermediate portion 62 of the applicator tip 24 to provide a secure anchoring technique for the applicator tip 24.

In order to manufacture an assembly embodying the principles of the present invention, the fibres of the shaft 22 are looped around the applicator tip 24, in the form described above. The fibres are then laid up in an appropriate orientation in a mould for the shaft 22. Liquid resin is then introduced into the mould in order to form the desired shape. The resin extends into the annular slot 70, thereby surrounding the fibres 56 extending into the slot 70. The mould is then evacuated of air, and the resin cured, in conventional manner. The resulting structure provides the elongate shaft 22, having an end closed by an applicator tip 24 securely fastened to the shaft 22.

As mentioned, the fibres of the shaft 22 may be of glass, aramid or carbon. For the case of non-electrically conductive fibres (glass, aramid), the applicator tip 24 may be of any material. Carbon fibres are electrically conductive, and so when carbon fibres are used form the body, the applicator tip 24 must be of a non-conductive material, for example, zirconia ceramic.

Figure 4:
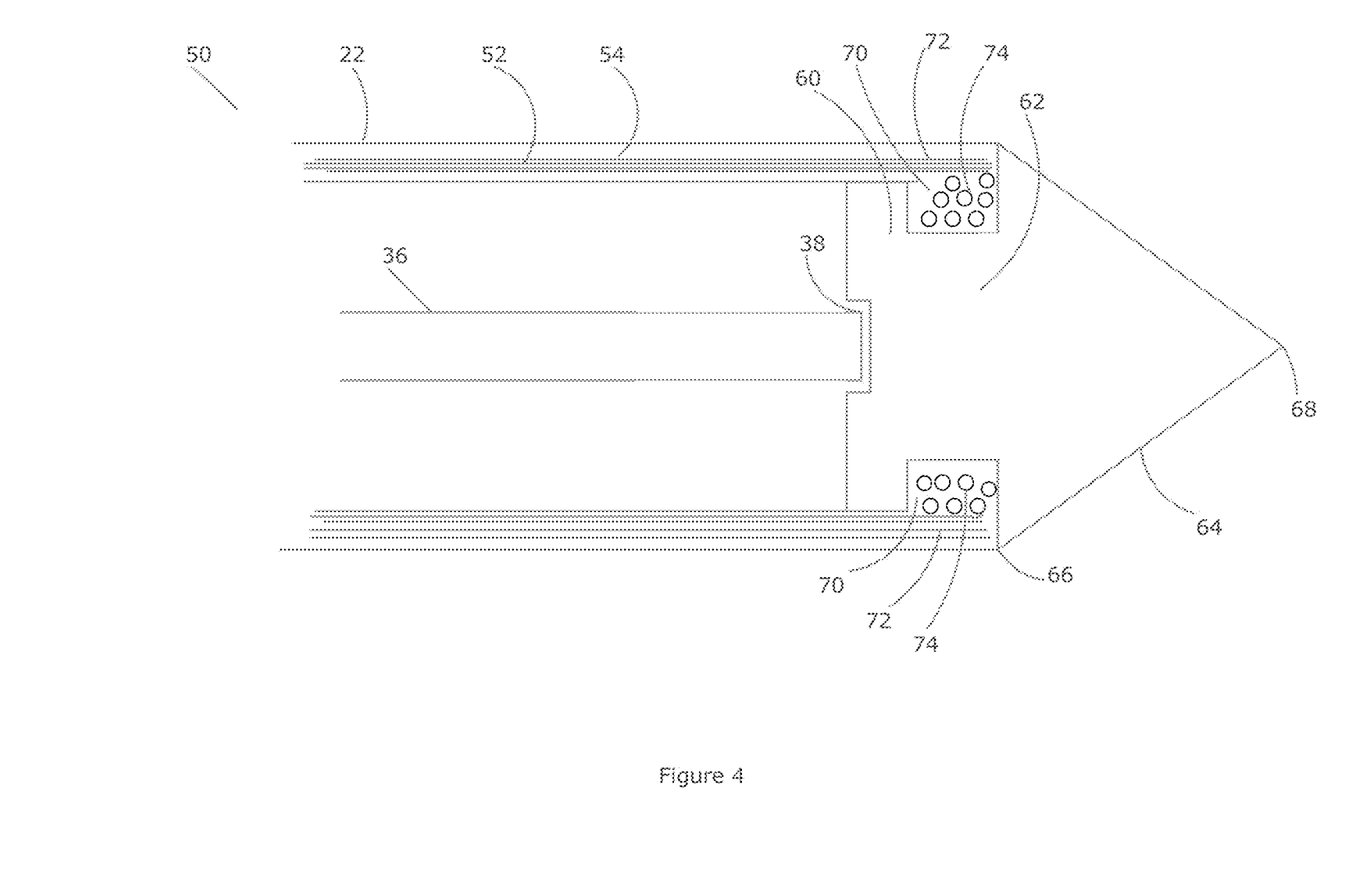

FIG. 4 illustrates an embodiment of the present invention that utilises an alternative arrangement for the attachment of the applicator tip 24 onto the shaft. In the embodiment of FIG. 4, the fibres 52 of the shaft extend longitudinally to an end region 72 which is located radially outside the annular slot 70 of the applicator tip 24. Unlike in the FIG. 3 embodiment, the fibres do not extend into the annular slot 70. A plurality of inner retaining fibres 74 extend circumferentially within the annular slot 70. The retaining fibres 74 are laid up and bound in the polymer material 54 of the shaft fibres 52. In such a way, the end of the shaft 24 is provided with a protrusion that extends into the annular slot 70 of the applicator tip 24, thereby securing the tip to the shaft.

Figure 5:
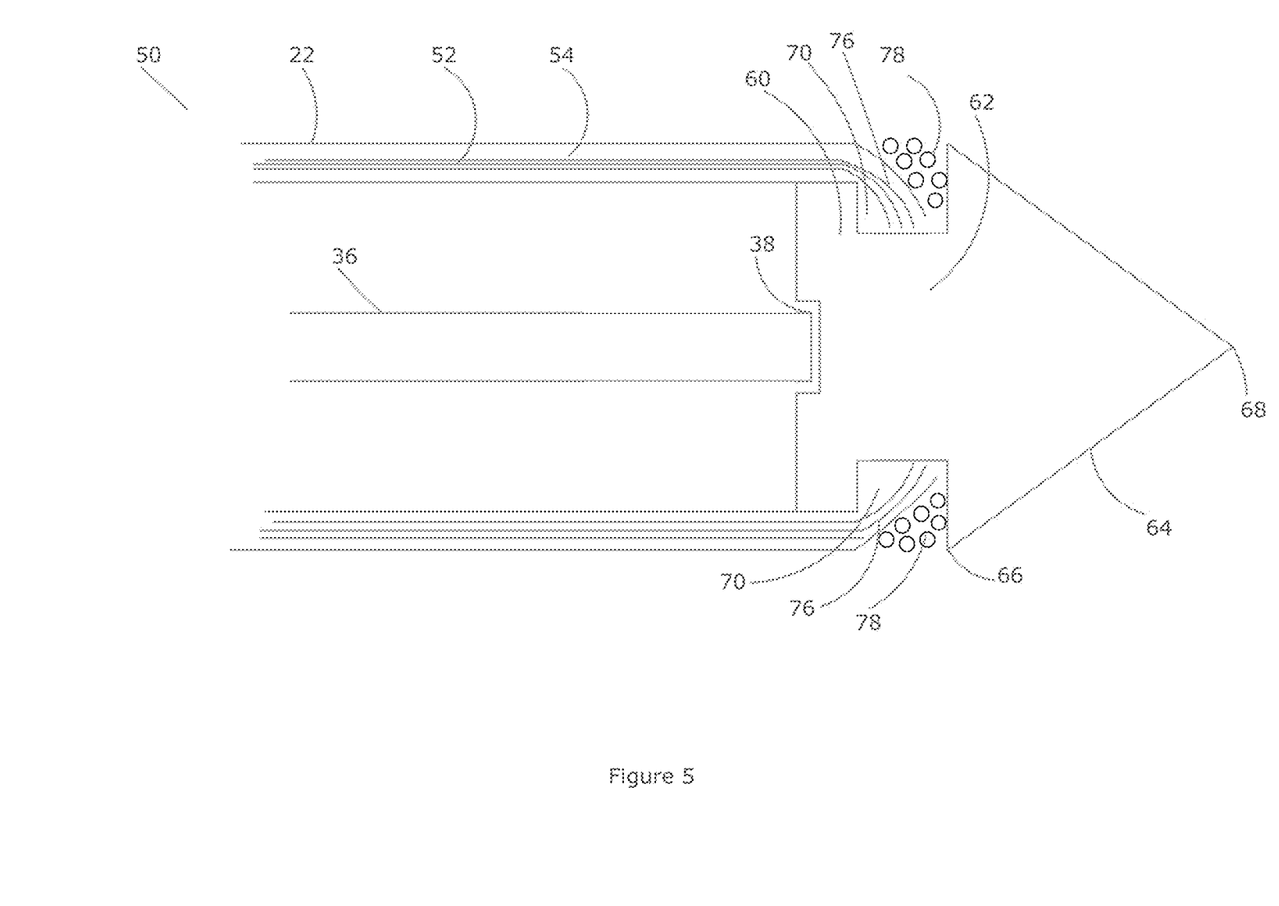

FIG. 5 illustrates an embodiment of the present invention that utilises another alternative arrangement for the attachment of the applicator tip 24 onto the shaft. In the embodiment of FIG. 5, the fibres 52 of the shaft extend to an end region 76 in the annular slot 70 of the applicator tip 24. A plurality of external retaining fibres 78 extend circumferentially within the annular slot 70. The external retaining fibres 74 are laid up and bound in the polymer material 54 of the shaft fibres 52. In such a way, the end of the shaft 24 is provided with a protrusion 76 that extends into the annular slot 70 of the applicator tip 24, thereby securing the tip to the shaft.

The invention claimed is:

1. A shaft assembly for a microwave ablation applicator which includes a shaft assembly and an antenna assembly located within the shaft assembly, the shaft assembly comprising:
   an elongate shaft which extends from a first end to a second end thereof, and which defines therein a hollow inner volume and a longitudinal axis of the antenna assembly; and
   an applicator tip mounted on the second end of the elongate shaft,
   wherein the applicator tip of the shaft assembly defines an annular slot with which the second end of the elongate shaft engages, and
   wherein at least a part of the shaft is of a fibre reinforced plastics material having a plurality of elongate fibres bound in a plastics material, at least some of the fibres extending at least partially circumferentially in and around the annular slot of the applicator tip.

2. An assembly as claimed in claim 1, wherein at least some of the fibres extend along the elongate shaft substantially parallel to the longitudinal axis of the antenna assembly, those fibres extending into and at least partially around the annular slot in the applicator tip.

3. An assembly as claimed in claim 1, wherein at least some of the fibres extend along the elongate shaft substantially parallel to the longitudinal axis of the antenna assembly, those fibres extending into and at least partially around the annular slot in the applicator tip, and wherein at least some of the fibres extend substantially circumferentially fully around the annular slot in the applicator tip.

4. An assembly as claimed in claim 1, wherein at least some of the fibres extend along the elongate shaft substantially parallel to the longitudinal axis of the antenna assembly, those fibres extending into and at least partially around the annular slot in the applicator tip, and wherein substantially all of those fibres extend into the annular slot.

5. An assembly as claimed in claim 1, wherein at least some of the fibres extend along the elongate shaft substantially parallel to the longitudinal axis of the antenna assembly, those fibres extending into and at least partially around the annular slot in the applicator tip, and wherein substantially all of those fibres extend into the annular slot, and wherein substantially all of the fibres extend substantially circumferentially fully around the annular slot in the applicator tip.

6. An assembly as claimed in claim 1, wherein the at least some of the fibres that extend at least partially circumferentially in and around the annular slot of the applicator tip are distinct from the elongate fibres of the shaft to provide retaining fibres for the assembly.

7. An assembly as claimed in claim 1, wherein the at least some of the fibres that extend at least partially circumferentially in and around the annular slot of the applicator tip are distinct from the elongate fibres of the shaft to provide retaining fibres for the assembly, and wherein the retaining fibres extend circumferentially around the annular slot radially inside the fibres of the shaft.

8. An assembly as claimed in claim 1, wherein the at least some of the fibres that extend at least partially circumferentially in and around the annular slot of the applicator tip are distinct from the elongate fibres of the shaft to provide retaining fibres for the assembly, and wherein the retaining fibres extend circumferentially around the annular slot radially outside the fibres of the shaft.

9. An assembly as claimed in claim 1, wherein the at least some of the fibres that extend at least partially circumferentially in and around the annular slot of the applicator tip are distinct from the elongate fibres of the shaft to provide retaining fibres for the assembly, and wherein the retaining fibres are bound in the plastics material of the shaft fibres.

10. An assembly as claimed claim 1, wherein the fibre reinforced plastics material includes carbon fibres, and the applicator tip is of an electrically insulating material.

11. An assembly as claimed claim 1, wherein the applicator tip comprises a base portion which engages an internal surface of the elongate shaft, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion.

12. An assembly as claimed in claim 1, wherein the applicator tip comprises a base portion which engages an internal surface of the elongate shaft, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion, and wherein the base portion, intermediate portion, and distal portion of the applicator tip are provided by a single contiguous component.

13. A microwave ablation applicator comprising a shaft assembly and an antenna assembly located within the shaft assembly:
   the shaft assembly comprising an elongate shaft which extends from a first end to a second end thereof, and which defines therein a hollow inner volume and a longitudinal axis of the antenna assembly; and an applicator tip mounted on the second end of the elongate shaft, wherein the applicator tip of the shaft assembly defines an annular slot with which the second end of the elongate shaft engages, and wherein at least a part of the shaft is of a fibre reinforced plastics material having a plurality of elongate fibres bound in a plastics material, at least some of the fibres extending at least partially circumferentially in and around the annular slot of the applicator tip;
   the antenna assembly including an elongate coaxial conductor for connection to a source of microwave energy, the coaxial conductor extending from the first end of the shaft of the shaft assembly towards the second end of the shaft through the inner volume, the coaxial conductor having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the coaxial conductor at a distal end thereof towards the second end of the body elongate shaft, and a dipole tip portion which extends from the feed point of the coaxial conductor assembly towards the applicator tip of the shaft assembly, and which is electrically connected with the inner conductor of the coaxial conductor assembly.

14. An applicator tip for a shaft assembly as claimed in claim 1, wherein the applicator tip comprises a base portion for engagement with an internal surface of the elongate shaft, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion.

15. An applicator tip as claimed in claim 1, wherein the applicator tip comprises a base portion for engagement with an internal surface of the elongate shaft, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion, and wherein the base portion, intermediate portion, and distal portion of the applicator tip are provided by a single contiguous component.

* * * * *